(12) United States Patent
Sun et al.

(10) Patent No.: US 8,808,180 B2
(45) Date of Patent: Aug. 19, 2014

(54) PATIENT MONITOR HAVING ENTERTAINMENT FUNCTIONS AND CONTROL METHOD THEREOF

(75) Inventors: Shuo Sun, Shenzhen (CN); Xin Yin, Shenzhen (CN)

(73) Assignee: Edan Instruments, Inc., Shenzhen (CN)

( * ) Notice: Subject to any disclaimer, the term of this patent is extended or adjusted under 35 U.S.C. 154(b) by 0 days.

(21) Appl. No.: 13/133,949

(22) PCT Filed: May 26, 2010

(86) PCT No.: PCT/CN2010/073242
§ 371 (c)(1),
(2), (4) Date: Jun. 10, 2011

(87) PCT Pub. No.: WO2011/140721
PCT Pub. Date: Nov. 17, 2011

(65) Prior Publication Data
US 2012/0095299 A1 Apr. 19, 2012

(30) Foreign Application Priority Data

May 13, 2010 (CN) .......................... 2010 1 0175769

(51) Int. Cl.
*A61B 5/00* (2006.01)
*G06F 1/16* (2006.01)
*G06F 19/00* (2011.01)

(52) U.S. Cl.
CPC ................. *A61B 5/00* (2013.01); *G06F 1/1649* (2013.01); *G06F 19/3418* (2013.01)
USPC ............................ 600/301; 600/300; 345/428

(58) Field of Classification Search
USPC .................................. 600/300–301; 345/428
See application file for complete search history.

(56) References Cited

U.S. PATENT DOCUMENTS

| 4,051,522 A | 9/1977 | Healy et al. |
| 6,705,990 B1 * | 3/2004 | Gallant et al. ................ 600/300 |

(Continued)

FOREIGN PATENT DOCUMENTS

| CN | 201131117 Y | 10/2008 |
| CN | 201299557 Y | 9/2009 |

(Continued)

OTHER PUBLICATIONS

International Search Report for PCT application PCT/CN2010/073242 and English translation.

(Continued)

*Primary Examiner* — Bill Thomson
*Assistant Examiner* — Bobby Soriano
(74) *Attorney, Agent, or Firm* — Garcia-Zamor IP Law; Ruy M. Garcia-Zamor

(57) ABSTRACT

The disclosure provides a patient monitor having entertainment functions and a control method thereof. If a user initiates the entertainment functions of the patient monitor having entertainment functions, a system thereof sends an entertainment signal to an entertainment signal processing unit, the entertainment signal is then processed to display an image on an entertainment specific display apparatus, and sound playing is achieved via an entertainment specific loudspeaker. The system sends a parameter signal to a parameter signal processing unit in real time, the parameter signal is then processed to display real-time measurement values and waveforms of parameters on a monitor specific display apparatus, and playing of various sounds is achieved via a monitor specific loudspeaker. An alarm processing unit detects, in real-time, whether the physiological characteristics of patient meet the alarm condition, and once the condition is met, alarm is triggered immediately. With the patient monitor of the disclosure, patients can enjoy some entertainment activities for mental relaxation while lying on the bed without having an impact on normal real-time monitor for patients.

2 Claims, 6 Drawing Sheets

(56) References Cited

U.S. PATENT DOCUMENTS

| | | | |
|---|---|---|---|
| 6,968,375 B1* | 11/2005 | Brown | 709/224 |
| 7,233,781 B2* | 6/2007 | Hunter et al. | 455/404.1 |
| 8,068,104 B2* | 11/2011 | Rampersad | 345/440 |
| 2006/0082518 A1* | 4/2006 | Ram | 345/1.1 |
| 2007/0135688 A1* | 6/2007 | Brown | 600/300 |
| 2007/0255116 A1* | 11/2007 | Mehta et al. | 600/300 |
| 2007/0275690 A1* | 11/2007 | Hunter et al. | 455/404.2 |
| 2008/0004904 A1* | 1/2008 | Tran | 705/2 |
| 2008/0194918 A1 | 8/2008 | Kulik et al. | |
| 2009/0048493 A1* | 2/2009 | James et al. | 600/300 |
| 2010/0115548 A1 | 5/2010 | Leyvi | |
| 2011/0216064 A1* | 9/2011 | Dahl et al. | 345/428 |

FOREIGN PATENT DOCUMENTS

| | | |
|---|---|---|
| CN | 101606396 A | 12/2009 |
| EP | 2111717 A | 10/2009 |
| GB | 2446516 A | 8/2008 |
| JP | 2010517656 T | 5/2010 |
| WO | WO2008096286 A | 8/2008 |

OTHER PUBLICATIONS

Written Opinion of International Searching Authority for PCT application PCT/CN2010/073242 and English translation.

\* cited by examiner

PATIENT MONITOR HAVING ENTERTAINMENT FUNCTIONS AND CONTROL METHOD THEREOF

TECHNICAL FIELD

The disclosure relates to medical diagnosis instruments, specifically to a patient monitor having entertainment functions and a control method thereof.

BACKGROUND ART

Monitor is a common patient monitor apparatus in medical institutions that can monitor vital signs of a patient in real-time and will alarm in the acoustic and visual form in order to notify medical staffs upon the abnormal vital signs of the patient. The apparatus can be applied to the environments including a intensive care unit and a general ward.

The monitored patients in the intensive care unit and the general ward, who are conscious, are completely able to enjoy some entertainment activities, including watching television and listening to music. Moreover, long-time emptiness is extremely unbearable to the monitor-applied patients who are put to long-term monitor in general. In addition, people accompany the patients can also relax through entertainment functions while the patients are unconscious or have a rest. Based on such a background, the disclosure comes up to solve the problems that actually happen during patient monitor.

Chinese patent filed with the publication number CN101606386 and entitled patient entertainment system having patient specificity supplementary medical contents discloses a medical information transfer system configured to be cooperative with an entertainment device, the entertainment device is configured to present an entertainment audio/video content data stream, the medical information transfer system comprises: a multiplexer for inserting additional content into the entertainment audio/video content data stream; and a controller for selecting patient specificity contents to be inserted into the entertainment audio/video content data stream. A medical information transfer method comprises the steps of: presenting the entertainment audio/video content data stream via the entertainment device; and presenting the patient specificity contents via the entertainment device and the entertainment audio/video content data stream; the medical information transfer system configured to be cooperative with the entertainment device enables the entertainment device to be configured to present the entertainment audio/video content data stream, the medical information transfer system comprises: a module for inserting additional content into the entertainment audio/video content data stream; and a module for selecting the patient specificity contents to be inserted into the entertainment audio/video content data stream; the insertion module comprises the multiplexer and the selection module comprises a selection controller; the module for selecting the patient specificity contents determines the priority of the patient specificity contents and selects the patient specificity contents to be inserted based on the content priority, the controller comprises: a wireless transmitter which is simulated and configured to control the wireless output of a handheld remote controller of the entertainment device; the multiplexer is configured to insert the additional content into a designated channel of the entertainment audio/video content data stream, the controller is configured to simulate that the entertainment device displays the wireless output of the designated channel; the controller is configured to simulate that the entertainment device displays the wireless output of the designated channel in one of a sub-window and a main window; and the multiplexer is configured to insert the additional content as a text which is superposed on the presented video of the entertainment audio/video content data stream.

Also, Chinese patent filed with the publication number CN1191142 and entitled medical device having user interface suitable for house or limited nursing environment discloses a system controlling a medical apparatus by an entertainment display. In the normal treatment process, patients can watch the programs (e.g. television programs) on the entertainment display. In case of emergency, the medical apparatus can interrupt the entertainment program and enable the entertainment display to display the information related to the operation or state of the medical apparatus. The medical apparatus can also comprise a user input apparatus so that patients can move one selector image displayed by the entertainment display in order to control the medical apparatus.

The systems described above have the following defects: first of all, the systems do not have the function of alarm in case of physical abnormality of the monitored patients; secondly, the systems cannot provide entertainment function while displaying the indexes of physiological parameters of patients in real-time; and thirdly, the systems can only provide the monitor for single parameter but not on other parameters.

CONTENTS OF THE INVENTION

In order to solve the defects in the prior art, the disclosure provides a patient monitor having entertainment functions, which can provide entertainment functions for patients, does not delay the real-time monitor for patients and can remove the emptiness of patient during free time. The disclosure also provides a control method of the patient monitor.

The disclosure provides a patient monitor device having entertainment functions. The patient monitor device comprises a signal acquisition unit for acquiring external input signals, a signal reception unit for receiving the acquired signals, a master control unit for completing the assignment of the received signals, a particular signal processing unit for processing different assigned signals, a storage unit for selectively storing the information of the particular signal processing unit and an audio and video output unit for outputting the particular signals.

The signal acquisition unit comprises an entertainment signal acquisition unit for acquiring an entertainment signal and a physiological parameter signal acquisition unit for acquiring the physiological characteristics of monitored patients.

The particular signal processing unit comprises an entertainment signal processing unit for processing the signals acquired by the an entertainment signal acquisition unit, a parameter signal processing unit for processing the information of the physiological parameters acquired by the physiological parameter signal acquisition unit, and an alarm signal processing unit for judgment according to the processing result of the parameter signal processing unit.

The entertainment signal processing unit comprises an entertainment signal reception unit, an entertainment apparatus initiation unit and a signal judgment unit. The entertainment signal data is received by the entertainment signal reception unit and is then differentiated by the signal judgment unit in order to determine whether the data is single audio signal data, or single video signal data or the data of both audio and video. An apparatus initiating signal is input to the corresponding audio and video output unit according to the result of the signal judgment unit.

The audio and video output unit comprises a monitor specific display apparatus and a monitor specific loudspeaker which are connected with a signal output end of the alarm signal processing unit, and an entertainment specific playing display apparatus and an entertainment specific loudspeaker which are connected with the entertainment apparatus initiation unit.

The alarm signal processing unit for processing the alarm information of the physiological characteristics comprises an alarm detection unit for detecting the values of the physiological characteristics, an alarm judgment unit embedded with a threshold of physiological characteristic, an alarm initiation controlling unit connected with a control signal output end of the alarm judgment unit, and an alarm storage unit for storing the information of the occurring alarm and the current parameter measurement values. The alarm detection unit detects the values of the physiological characteristics in real-time. The alarm judgment unit judges whether alarm occurs, and if the alarm occurs, the alarm initiation controlling unit initiates an alarm lamp, an alarm specific loudspeaker and a screen character prompt; If the alarm is finished, the alarm storage unit stores the information of the occurring alarm and the current parameter measurement values. Once the alarm condition disappears, the alarm in any form is canceled.

In the patient monitor having entertainment functions, the system thereof sends an entertainment signal to the entertainment signal processing unit if an user initiates the entertainment functions, the entertainment signal is then processed to display an image on the entertainment specific display apparatus, and sound playing is achieved via the entertainment specific loudspeaker.

The system sends a parameter signal to the parameter signal processing unit in real time, the parameter signal is then processed to display real-time measurement values and waveforms of parameters on the monitor specific display apparatus, and playing of various sounds is achieved via the monitor specific loudspeaker.

The alarm processing unit detects, in real-time, whether the physiological characteristics of patient meet the alarm condition, and once the condition is met, alarm is triggered immediately. If the entertainment function and the alarm function are simultaneously used, the entertainment specific loudspeaker is muted and the monitor specific loudspeaker gives alarm sound when the abnormal vital signs of patient trigger the alarm, however, no impact is applied to the contents displayed on the entertainment specific display.

With the disclosure, the patients can enjoy some entertainment activities for mental relaxation while lying on the bed without having an impact on normal real-time monitor for patients.

The entertainment signal acquisition unit comprises a television signal acquisition unit for acquiring television signals, a broadcast signal acquisition unit for acquiring broadcast signals, a network signal acquisition unit for acquiring network signals and a disc video/audio signal acquisition unit for acquiring disc video/audio signals.

The patient monitor having entertainment functions further comprises a remote control command receiving/transmitting and operating device in signal interaction with the signal reception unit, for transmitting a remote control command or receiving a state signal returned by the signal reception unit.

The remote control command receiving/transmitting and operating device is a handheld mobile terminal having wireless application communication protocol, and the handheld mobile terminal is provided with an authorized digital certificate uniquely corresponding thereto.

The control command reception and processing module is a wireless application communication protocol server which can receive the signal of the handheld mobile terminal through wireless network. The wireless application communication protocol server includes a wireless application communication certificate module for issuing and verifying digital certificates, a wireless storage module for storing different mode commands, a wireless address book module for storing the assigned address of control device for electric and electrical equipment, an operating interface offering module for offering a service interface, a wireless state detection module for feeding back and updating the current state of the controlled electric and electrical equipment in real-time, a wireless application communication protocol server data mirror backup module for backing up the wireless application communication protocol server data in real-time, and a power line carrier control signal module for transmitting the control signal, resulted from the processing of the wireless application communication protocol server, to a signal transmission network in a manner of carrier.

The remote control command receiving/transmitting and operating device is a handheld mobile terminal having the function of hypertext transfer protocol, and the handheld mobile terminal is provided with an authorized digital certificate uniquely corresponding thereto.

The control command reception and processing module is a WEB server which can receive the signal of the handheld mobile terminal through wireless network. The wireless application communication protocol server includes a WEB server certificate module for issuing and verifying digital certificates, a WEB storage module for storing different mode commands, a WEB address book module for storing the assigned address of control device for electric and electrical equipment, an operating interface offering module for offering a service interface, a WEB state detection module for feeding back and updating the current state of the controlled electric and electrical equipment in real-time, a WEB server data mirror backup module for backing up the WEB server data in real-time, and a power line carrier control signal module for transmitting the control signal, resulted from the processing of the WEB server, to a signal transmission network in a manner of carrier.

The remote control command receiving/transmitting and operating device can be connected with a computer in a remote network.

The control command reception and processing module is a remote host server connected to the remote network. The remote host server includes a verification module for issuing and verifying ID at an IP login port, a storage module for storing different mode commands, an address book module for storing the assigned address of control device for electric and electrical equipment, an interface offering module for offering a service interface, a state detection module for feeding back and updating the current state of the controlled electric and electrical equipment in real-time, a remote host server data mirror backup module for backing up the host server data in real-time, and a power line carrier control signal module for transmitting the control signal, resulted from the processing of the remote host server, to a signal transmission network in a manner of carrier.

The remote control command receiving/transmitting and operating device is an intelligent learning-type remote controller having infrared/radio frequency transmission and reception functions.

The intelligent learning-type remote controller comprises a central processing unit, and a keyboard, a display unit, a wireless communication unit and a storage unit which are connected with the central processing unit. The storage unit is used for storing description files of the household appliances. The wireless communication unit comprises an infrared module for code matching learning with controlled electric and electrical equipment having infrared recognition control function and a radio frequency module for transmitting a control command. The keyboard and the display unit are used for offering a man-machine interactive interface.

The control command reception and processing module in the control command reception and processing device is a reception module capable of receiving infrared/radio frequency signals.

The monitor specific display apparatus and the entertainment specific display apparatus are double-screen display apparatuses. The double-screen display apparatus comprises a first display panel including a monitor specific display screen, a second display panel including an entertainment specific display screen and a connection shaft for the connection of the two display panels. The connection shaft comprises a first shaft component rotatably pivoted to the first display panel and a second shaft component rotatably coupled to the second display panel. The second shaft component extends from the first shaft component so as to be vertical to the first shaft component. The connection shaft is connected to one corner of the first display panel and one corner of the second display panel. The double-screen display apparatus further comprises a first shaft accommodation groove formed at the second display panel to receive a part of the first shaft component, a second shaft accommodation groove formed at the first display panel to receive a part of the second shaft component, and at least one magnet assembled at the edge of the first display panel and the second display panel so that the first display panel and the second display panel can be adhered to each other.

The double-screen display apparatus comprises an external adapter module, a loop module, a display module and a signal input module. The loop module comprises a boosting board and a micro-control processor, the external adapter module supplies power to the boosting board and the micro-control processor. The display module comprises a first display panel and a second display panel as well as provides working voltage for the boosting board and simultaneously receives and displays the signals provided by the micro-control processor, the signal input module is connected with the micro-control processor, and the micro-control processor processes the signals input by the signal input module and controls the first display panel and the second display panel respectively.

The double-screen display apparatus comprises combination sensors which are correspondingly installed on the corresponding positions of the first display panel and the second display panel respectively and which sense whether the two display panels are combined. The combination sensors are in signal interaction with the micro-control processor. The micro-control processor further comprises a combination image processing unit in signal interaction with the combination sensors, and a combination image selecting unit in signal interaction with the combination image processing unit for inputting the selected signals.

When the combination sensors sense that the two display panels are at a combination position, the combination image processing unit regulates an original single-screen display resolution to a combined screen display resolution which is suitable for double-screen combination, and simultaneously, according to the selected signals input by a user through the combination image selecting unit, original display contents on the original first or second display panel are taken as the display contents of the entire screen subsequent to combination.

The double-screen display apparatus comprises combination sensors which are correspondingly installed on the corresponding positions of the first display panel and the second display panel respectively and which sense whether the two display panels are combined. The combination sensors are in signal interaction with the micro-control processor. The micro-control processor further comprises a combination image processing unit in signal interaction with the combination sensors, and a combination image judging and selecting unit in signal interaction with the entertainment signal processing unit and a parameter signal processing unit as well as the combination sensors.

When the combination sensors sense that the two display panels are at the combination position, the combination image processing unit regulates an original single-screen display resolution to a combined screen display resolution which is suitable for double-screen combination; and simultaneously, according to the judged and selected signals from the combination image judging and selecting unit, original display contents on the original first or second display panel, are taken as the display contents of the entire screen subsequent to combination. When the position of the second display panel for displaying entertainment contents is changed and the position of the first display panel for displaying the information of physiological characteristics of patient is unchanged, the original contents on the first display panel are displayed subsequent to combination.

When the position of the first display panel for displaying the information of physiological characteristics of patient is changed and the position of the screen for displaying entertainment contents is not changed, the original contents displayed on the second display panel are displayed subsequent to combination.

The control method of the patient monitor having entertainment functions comprises following steps.

A user initiates the patient monitor having entertainment functions so that patient is put into monitor and various values of the physiological characteristics and wave curves of patient are displayed on the monitor specific screen.

The user selects the entertainment function according to own requirement.

A particular entertainment function is activated, and a particular entertainment signal is acquired via a corresponding signal acquisition unit and then processed.

Whether an alarm is performed is judged according to various values of the physiological parameters of the monitored patient.

If the alarm should be performed according to the judgment, the loudspeaker for entertainment is shut off and the monitor specific loudspeaker alarms.

If the alarm should not be performed according to the judgment, the specific entertainment apparatus continues operating.

The patient monitor having entertainment functions is shut down after the use thereof.

Further, the patient monitor shuts off the alarm specific loudspeaker and reinitiates the entertainment apparatus after the parameters of the monitored patient return to be normal and the alarm is canceled.

The control method of the patient monitor having entertainment functions further comprises: judging a received multimedia signal; converting the received data into a data format required by the loudspeaker and initiating the entertainment specific loudspeaker in case of single audio signal;

converting the received data into a data format required by the display apparatus and initiating the entertainment specific display apparatus in case of single video signal; and converting the received data into data formats required by the loudspeaker and the display apparatus and initiating the entertainment specific loudspeaker and the entertainment specific display apparatus in case of both audio signal and video signal.

The control method of the patient monitor having entertainment functions further comprises following steps.

A real-time physiological signal is subjected to alarm judgment, including the judgment for higher limit and lower limit of alarm, the judgment for arrhythmia alarm and the judgment for asphyxia or cardiac arrest alarm.

If the alarm condition is met, the alarm is initiated, and doctor or nurse is reminded of the timely treatment for the monitored patient in a manner of character prompt on screen by turning on alarming lamp and alarm loudspeaker. After the alarm, the system stores the alarm occurring so as to facilitate reviewing and knowing history alarms of the patient in time. During the alarm, the system detects the alarm state of the monitored patient in real-time, and once the patient is physically stable so as not to meet the alarm condition, the system stops the current alarm in any form.

The entertainment apparatus in the control method comprises the entertainment specific loudspeaker and the entertainment specific display apparatus.

In the patient monitor having entertainment functions, the system thereof sends an entertainment signal to the entertainment signal processing unit if user initiates the entertainment functions, the entertainment signal is then processed to display an image on the entertainment specific display apparatus, and sound playing is achieved via the entertainment specific loudspeaker.

The system sends a parameter signal to the parameter signal processing unit in real time, the parameter signal is then processed to display real-time measurement values and waveforms of parameters on the monitor specific display apparatus, and playing of various sounds is achieved via the monitor specific loudspeaker.

The alarm processing unit detects, in real-time, whether the physiological characteristics of patient meet the alarm condition, and once the condition is met, alarm is triggered immediately. If the entertainment function and the alarm function are simultaneously used, the entertainment specific loudspeaker is muted and the monitor specific loudspeaker gives alarm sound when the abnormal vital signs of patient trigger the alarm, however, no impact is applied to the contents displayed on the entertainment specific display.

With the disclosure, the patients can enjoy some entertainment activities for mental relaxation while lying on the bed without having an impact on normal real-time monitor for patients.

MODE OF CARRYING OUT THE INVENTION

For better understanding the purpose, technical proposal and advantages of the invention, detailed description is further made below to the invention with reference to the drawings and the embodiments. It will be appreciated that, the embodiments described herein are merely explanation, not limitation to the invention.

Figure 2:
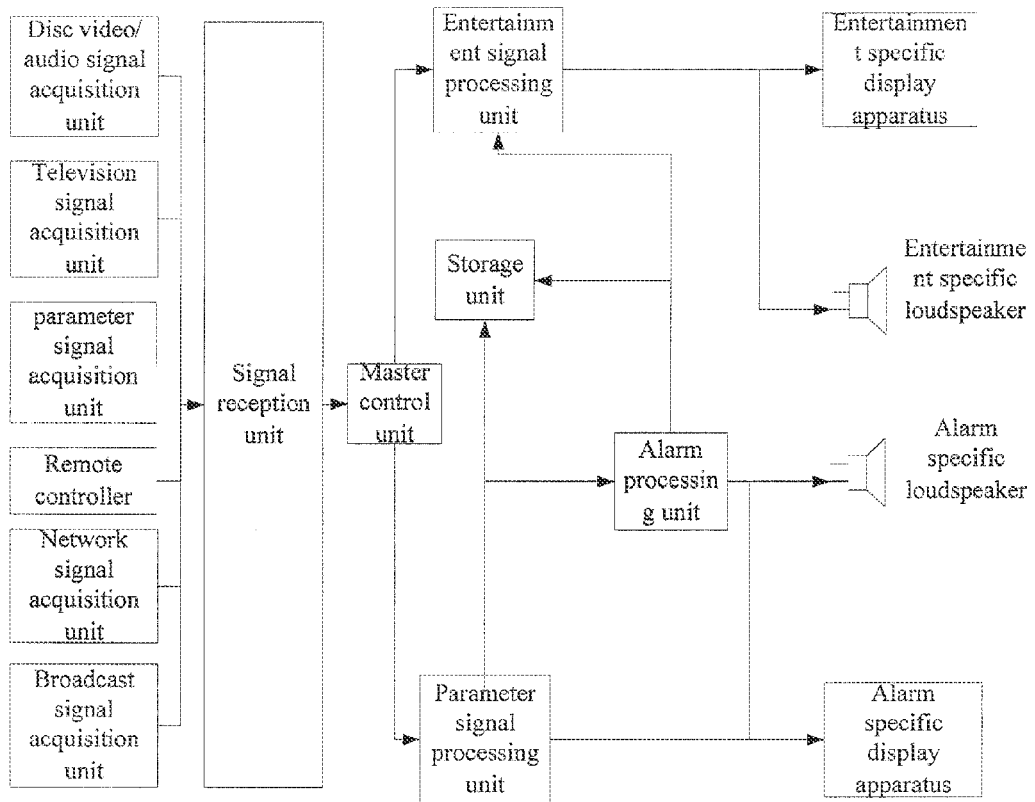
FIG. 2 is a block diagram of the structural system of the patient monitor having entertainment functions of the disclosure.
Figure 3:
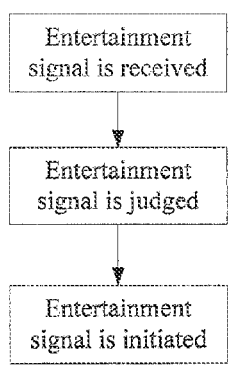
FIG. 3 is a flow chart of the specific steps in the step 3.
Figure 4:
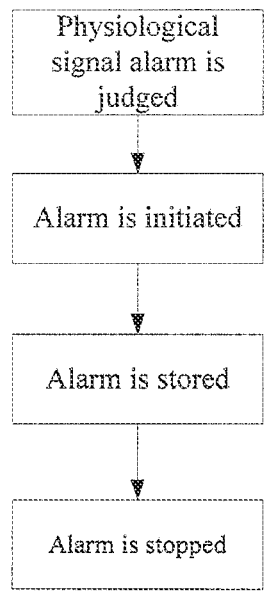
FIG. 4 is a flow chart of the specific steps in the step 5.
Figure 5:
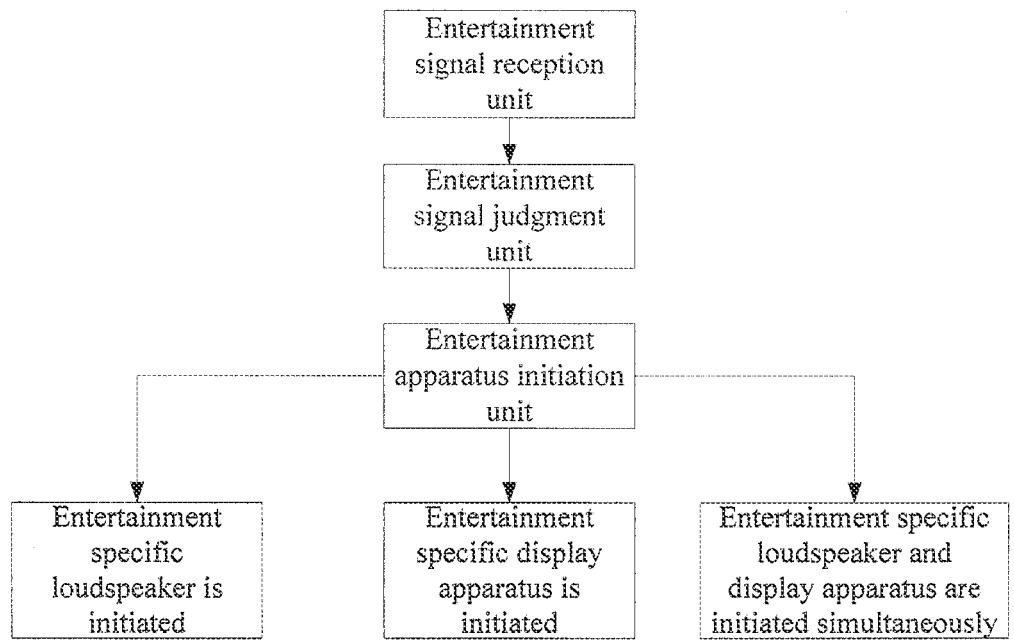
FIG. 5 is a block diagram of an internal structure of an entertainment signal processing unit of a medical monitor having entertainment functions in FIG. 2.
Figure 6:
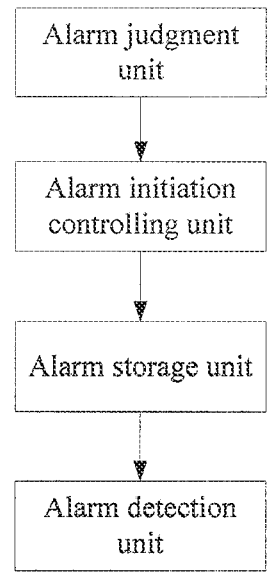
FIG. 6 is a block diagram of an internal structure of an alarm signal processing unit of the medical monitor having entertainment functions in FIG. 2.
Figure 7:
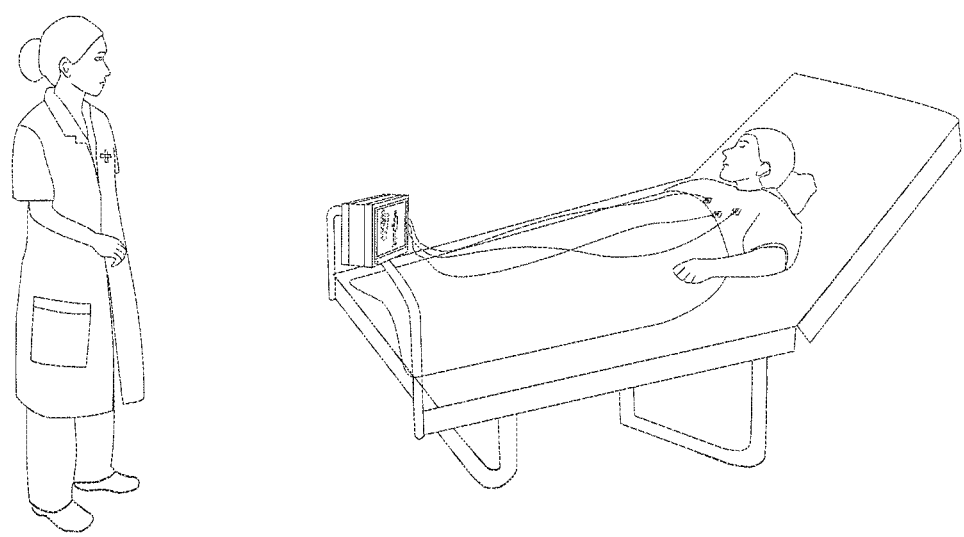
FIG. 7 is a schematic diagram of an using state of the patient monitor having entertainment functions in FIG. 2.
Figure 8:
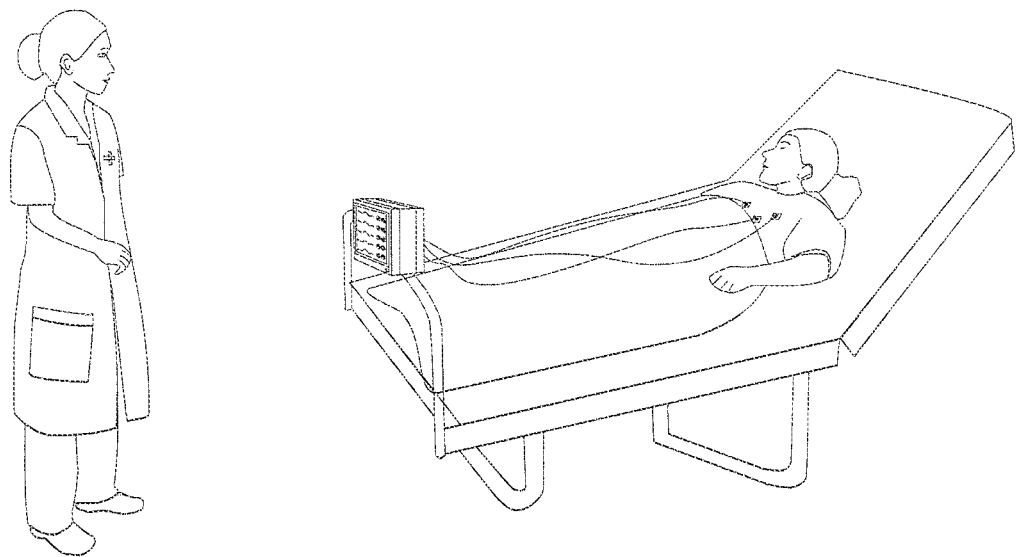
FIG. 8 is a schematic diagram of another using state of the patient monitor having entertainment functions in FIG. 2.

With reference to FIGS. 2, 5 and 6, a patient monitor having entertainment functions comprises a signal acquisition unit for acquiring external input signals, a signal reception unit for receiving the acquired signals, a master control unit for completing the assignment of the received signals, a particular signal processing unit for processing different assigned signals, a storage unit for selectively storing the information of the particular signal processing unit and an audio and video output unit for outputting the particular signals.

The signal acquisition unit comprises an entertainment signal acquisition unit for acquiring an entertainment signal and a physiological parameter signal acquisition unit for acquiring the physiological characteristics of monitored patients.

The particular signal processing unit comprises an entertainment signal processing unit for processing the signals acquired by the an entertainment signal acquisition unit, a parameter signal processing unit for processing the information of the physiological parameters acquired by the physiological parameter signal acquisition unit, and an alarm signal processing unit for judgment according to the processing result of the parameter signal processing unit.

The entertainment signal processing unit comprises an entertainment signal reception unit, an entertainment apparatus initiation unit and a signal judgment unit. The entertainment signal data is received by the entertainment signal reception unit and is then differentiated by the signal judgment unit in order to determine whether the data is single audio signal data, or single video signal data or the data of both audio and video. An apparatus initiating signal is input to the corresponding audio and video output unit according to the result of the signal judgment unit.

The audio and video output unit comprises a monitor specific display apparatus and a monitor specific loudspeaker which are connected with a signal output end of the alarm signal processing unit, and an entertainment specific playing display apparatus and an entertainment specific loudspeaker which are connected with the entertainment apparatus initiation unit.

The alarm signal processing unit for processing the alarm information of the physiological characteristics comprises an alarm detection unit for detecting the values of the physiological characteristics, an alarm judgment unit embedded with a threshold of physiological characteristic, an alarm initiation controlling unit connected with a control signal output end of the alarm judgment unit, and an alarm storage unit for storing the information of the occurring alarm and the current parameter measurement values. The alarm detection unit detects the values of the physiological characteristics in real-time. The alarm judgment unit judges whether alarm occurs, and if the alarm occurs, the alarm initiation controlling unit initiates an alarm lamp, an alarm specific loudspeaker and a screen character prompt; If the alarm is finished, the alarm storage unit stores the information of the occurring alarm and the current parameter measurement values. Once the alarm condition disappears, the alarm in any form is canceled.

In the patient monitor having entertainment functions, the system thereof sends an entertainment signal to the entertainment signal processing unit if an user initiates the entertainment functions, the entertainment signal is then processed to display an image on the entertainment specific display apparatus, and sound playing is achieved via the entertainment specific loudspeaker.

The system sends a parameter signal to the parameter signal processing unit in real time, the parameter signal is then processed to display real-time measurement values and waveforms of parameters on the monitor specific display apparatus, and playing of various sounds is achieved via the monitor specific loudspeaker.

The alarm processing unit detects, in real-time, whether the physiological characteristics of patient meet the alarm condition, and once the condition is met, alarm is triggered immediately. If the entertainment function and the alarm function are simultaneously used, the entertainment specific loudspeaker is muted and the monitor specific loudspeaker gives alarm sound when the abnormal vital signs of patient trigger the alarm, however, no impact is applied to the contents displayed on the entertainment specific display.

With the disclosure, the patients can enjoy some entertainment activities for mental relaxation while lying on the bed without having an impact on normal real-time monitor for patients.

The entertainment signal acquisition unit comprises a television signal acquisition unit for acquiring television signals, a broadcast signal acquisition unit for acquiring broadcast signals, a network signal acquisition unit for acquiring network signals and a disc video/audio signal acquisition unit for acquiring disc video/audio signals.

The patient monitor having entertainment functions further comprises a remote control command receiving/transmitting and operating device in signal interaction with the signal reception unit, for transmitting a remote control command or receiving a state signal returned by the signal reception unit.

Alternatively, the remote control command receiving/transmitting and operating device is a handheld mobile terminal having wireless application communication protocol, and the handheld mobile terminal is provided with an authorized digital certificate uniquely corresponding thereto.

The control command reception and processing module is a wireless application communication protocol server which can receive the signal of the handheld mobile terminal through wireless network. The wireless application communication protocol server includes a wireless application communication certificate module for issuing and verifying digital certificates, a wireless storage module for storing different mode commands, a wireless address book module for storing the assigned address of control device for electric and electrical equipment, an operating interface offering module for offering a service interface, a wireless state detection module for feeding back and updating the current state of the controlled electric and electrical equipment in real-time, a wireless application communication protocol server data mirror backup module for backing up the wireless application communication protocol server data in real-time, and a power line carrier control signal module for transmitting the control signal, resulted from the processing of the wireless application communication protocol server, to a signal transmission network in a manner of carrier.

Alternatively, the remote control command receiving/transmitting and operating device is a handheld mobile terminal having the function of hypertext transfer protocol, and the handheld mobile terminal is provided with an authorized digital certificate uniquely corresponding thereto.

The control command reception and processing module is a WEB server which can receive the signal of the handheld mobile terminal through wireless network. The wireless application communication protocol server includes a WEB server certificate module for issuing and verifying digital certificates, a WEB storage module for storing different mode commands, a WEB address book module for storing the assigned address of control device for electric and electrical equipment, an operating interface offering module for offering a service interface, a WEB state detection module for feeding back and updating the current state of the controlled electric and electrical equipment in real-time, a WEB server data mirror backup module for backing up the WEB server data in real-time, and a power line carrier control signal module for transmitting the control signal, resulted from the processing of the WEB server, to a signal transmission network in a manner of carrier.

Alternatively, the remote control command receiving/transmitting and operating device can be connected with a computer in a remote network.

The control command reception and processing module is a remote host server connected to the remote network. The remote host server includes a verification module for issuing and verifying ID at an IP login port, a storage module for storing different mode commands, an address book module for storing the assigned address of control device for electric and electrical equipment, an interface offering module for offering a service interface, a state detection module for feeding back and updating the current state of the controlled electric and electrical equipment in real-time, a remote host server data mirror backup module for backing up the host server data in real-time, and a power line carrier control signal module for transmitting the control signal, resulted from the processing of the remote host server, to a signal transmission network in a manner of carrier.

Alternatively, the remote control command receiving/transmitting and operating device is an intelligent learning-type remote controller having infrared/radio frequency transmission and reception functions.

The intelligent learning-type remote controller comprises a central processing unit, and a keyboard, a display unit, a wireless communication unit and a storage unit which are connected with the central processing unit. The storage unit is used for storing description files of the household appliances. The wireless communication unit comprises an infrared module for code matching learning with controlled electric and electrical equipment having infrared recognition control function and a radio frequency module for transmitting a control command. The keyboard and the display unit are used for offering a man-machine interactive interface.

The control command reception and processing module in the control command reception and processing device is a reception module capable of receiving infrared/radio frequency signals.

The monitor specific display apparatus and the entertainment specific display apparatus are double-screen display apparatuses. The double-screen display apparatus comprises a first display panel including a monitor specific display screen, a second display panel including an entertainment specific display screen and a connection shaft for the connection of the two display panels. The connection shaft comprises a first shaft component rotatably pivoted to the first display panel and a second shaft component rotatably coupled to the second display panel. The second shaft component extends from the first shaft component so as to be vertical to the first shaft component. The connection shaft is connected to one corner of the first display panel and one corner of the second display panel. The double-screen display apparatus further comprises a first shaft accommodation groove formed at the second display panel to receive a part of the first shaft component, a second shaft accommodation groove formed at the first display panel to receive a part of the second shaft component, and at least one magnet assembled at the edge of the first display panel and the second display panel so that the first display panel and the second display panel can be adhered to each other.

The double-screen display apparatus comprises an external adapter module, a loop module, a display module and a signal input module. The loop module comprises a boosting board and a micro-control processor, the external adapter module supplies power to the boosting board and the micro-control processor. The display module comprises a first display panel and a second display panel as well as provides working voltage for the boosting board and simultaneously receives and displays the signals provided by the micro-control processor, the signal input module is connected with the micro-control processor, and the micro-control processor processes the signals input by the signal input module and controls the first display panel and the second display panel respectively.

The double-screen display apparatus comprises combination sensors which are correspondingly installed on the corresponding positions of the first display panel and the second display panel respectively and which sense whether the two display panels are combined. The combination sensors are in signal interaction with the micro-control processor. The micro-control processor further comprises a combination image processing unit in signal interaction with the combination sensors, and a combination image selecting unit in signal interaction with the combination image processing unit for inputting the selected signals.

Figure 9:
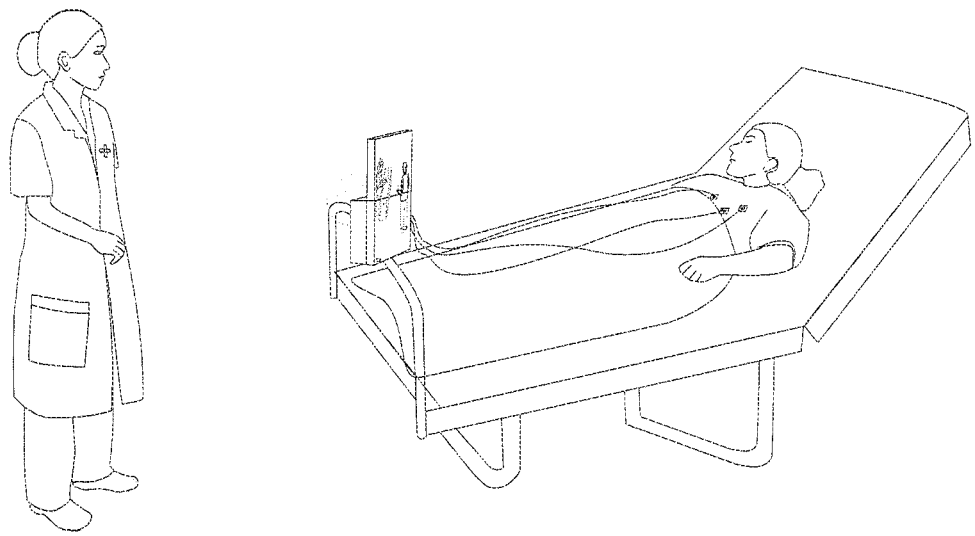
FIG. 9 is a schematic diagram of patient using combined screen during the use of the patient monitor having entertainment functions in FIG. 2.
Figure 10:
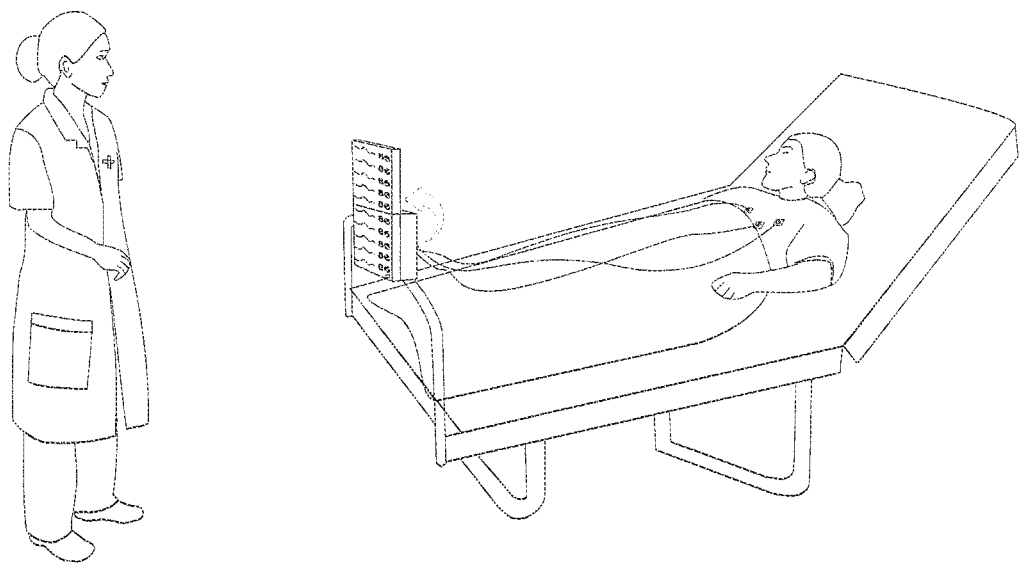
FIG. 10 is a schematic diagram of monitor doctor using combined screen during the use of the patient monitor having entertainment functions in FIG. 2.

With reference to FIGS. 9 and 10, when the combination sensors sense that the two display panels are at a combination position, the combination image processing unit regulates an original single-screen display resolution to a combined screen display resolution which is suitable for double-screen combination, and simultaneously, according to the selected signals input by a user through the combination image selecting unit, original display contents on the original first or second display panel are taken as the display contents of the entire screen subsequent to combination.

The double-screen display apparatus comprises combination sensors which are correspondingly installed on the corresponding positions of the first display panel and the second display panel respectively and which sense whether the two display panels are combined. The combination sensors are in signal interaction with the micro-control processor. The micro-control processor further comprises a combination image processing unit in signal interaction with the combination sensors, and a combination image judging and selecting unit in signal interaction with the entertainment signal processing unit and a parameter signal processing unit as well as the combination sensors.

With reference to FIGS. 9 and 10, when the combination sensors sense that the two display panels are at the combination position, the combination image processing unit regulates an original single-screen display resolution to a combined screen display resolution which is suitable for double-screen combination; and simultaneously, according to the judged and selected signals from the combination image judging and selecting unit, original display contents on the original first or second display panel are taken as the display contents of the entire screen subsequent to combination.

When the position of the second display panel for displaying entertainment contents is changed and the position of the first display panel for displaying the information of physiological characteristics of patient is unchanged, the original contents on the first display panel are displayed subsequent to combination.

When the position of the first display panel for displaying the information of physiological characteristics of patient is changed and the position of the screen for displaying entertainment contents is not changed, the original contents displayed on the second display panel are displayed subsequent to combination.

Figure 1:
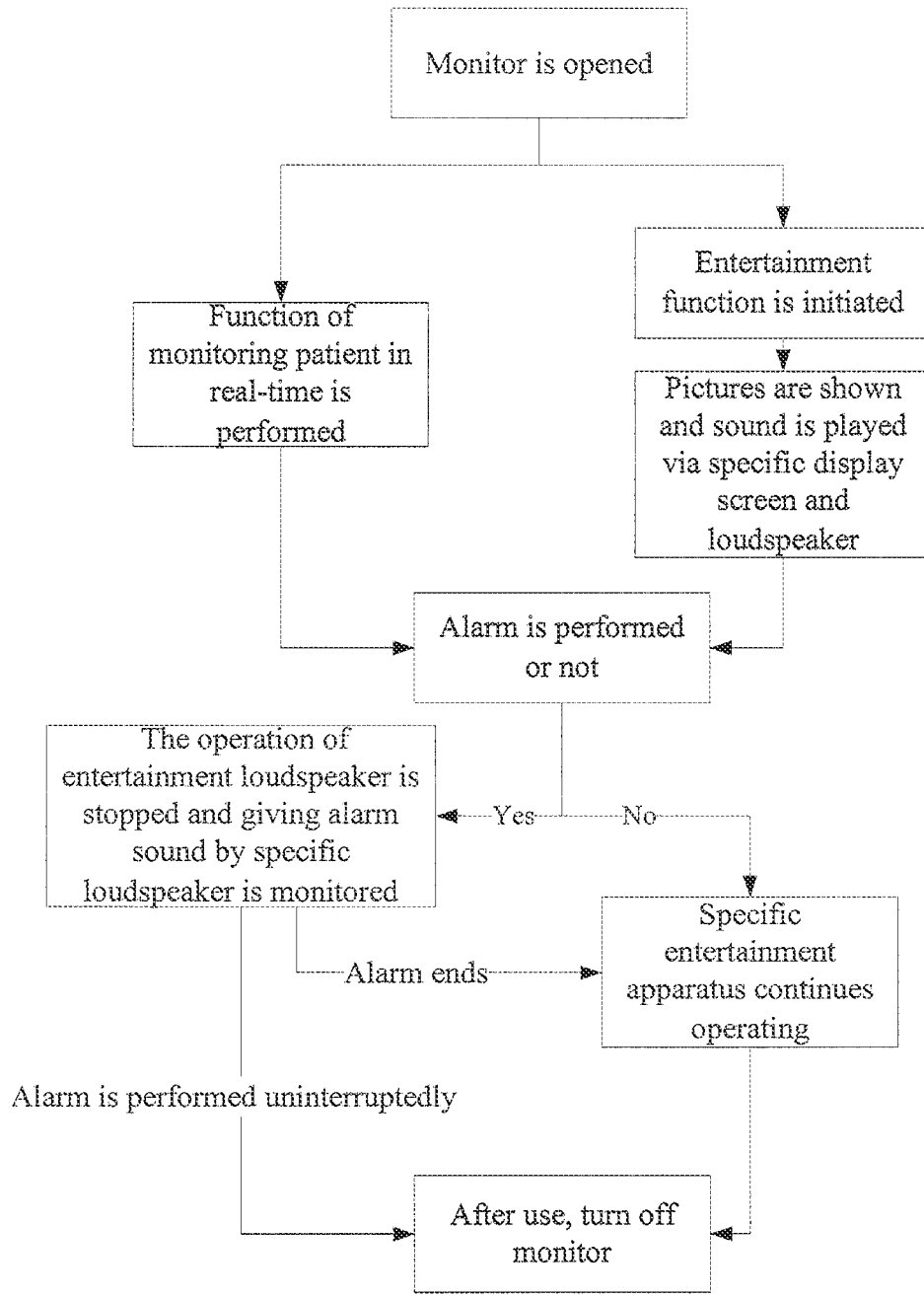
FIG. 1 is a flow chart of a control method of a patient monitor having entertainment functions of the disclosure.

Shown as FIG. 1, the control method of the patient monitor having entertainment functions comprises following steps.

A user initiates the patient monitor having entertainment functions so that patient is put into monitor and various values of the physiological characteristics and wave curves of patient are displayed on the monitor specific screen.

The user selects the entertainment function according to own requirement.

A particular entertainment function is activated, and a particular entertainment signal is acquired via a corresponding signal acquisition unit and then processed.

Whether an alarm is performed is judged according to various values of the physiological parameters of the monitored patient.

If the alarm should be performed according to the judgment, the loudspeaker for entertainment is shut off and the monitor specific loudspeaker alarms.

If the alarm should not be performed according to the judgment, the specific entertainment apparatus continues operating.

The patient monitor having entertainment functions is shut down after the use thereof.

Further, the patient monitor shuts off the alarm specific loudspeaker and reinitiates the entertainment apparatus after the parameters of the monitored patient return to be normal and the alarm is canceled.

The control method of the patient monitor having entertainment functions further comprises: judging a received multimedia signal; converting the received data into a data format required by the loudspeaker and initiating the entertainment specific loudspeaker in case of single audio signal; converting the received data into a data format required by the display apparatus and initiating the entertainment specific display apparatus in case of single video signal; and converting the received data into data formats required by the loudspeaker and the display apparatus and initiating the entertainment specific loudspeaker and the entertainment specific display apparatus in case of both audio signal and video signal.

The control method of the patient monitor having entertainment functions further comprises following steps.

A real-time physiological signal is subjected to alarm judgment, including the judgment for higher limit and lower limit of alarm, the judgment for arrhythmia alarm and the judgment for asphyxia or cardiac arrest alarm.

If the alarm condition is met, the alarm is initiated, and doctor or nurse is reminded of the timely treatment for the monitored patient in a manner of character prompt on screen by turning on alarming lamp and alarm loudspeaker. After the alarm, the system stores the alarm occurring so as to facilitate reviewing and knowing history alarms of the patient in time. During the alarm, the system detects the alarm state of the monitored patient in real-time, and once the patient is physically stable so as not to meet the alarm condition, the system stops the current alarm in any form.

The entertainment apparatus in the control method comprises the entertainment specific loudspeaker and the entertainment specific display apparatus.

In the patient monitor having entertainment functions, the system thereof sends an entertainment signal to the entertainment signal processing unit if user initiates the entertainment functions, the entertainment signal is then processed to display an image on the entertainment specific display apparatus, and sound playing is achieved via the entertainment specific loudspeaker.

The system sends a parameter signal to the parameter signal processing unit in real time, the parameter signal is then processed to display real-time measurement values and waveforms of parameters on the monitor specific display apparatus, and playing of various sounds is achieved via the monitor specific loudspeaker.

The alarm processing unit detects, in real-time, whether the physiological characteristics of patient meet the alarm condition, and once the condition is met, alarm is triggered immediately. If the entertainment function and the alarm function are simultaneously used, the entertainment specific loudspeaker is muted and the monitor specific loudspeaker gives alarm sound when the abnormal vital signs of patient trigger the alarm, however, no impact is applied to the contents displayed on the entertainment specific display.

With the disclosure, the patients can enjoy some entertainment activities for mental relaxation while lying on the bed without having an impact on normal real-time monitor for patients.

What is described above is merely the preferable embodiments, not limitation to the invention, any modifications, equivalent alternations and improvements without departing from the spirit and principal of the invention shall be within the scope of protection of the invention.

What is claimed is:

1. A patient monitor having entertainment functions, comprising:

a signal acquisition unit for acquiring external input signals, a signal reception unit for receiving the acquired signals, a master control unit for completing the assignment of the received signals, a particular signal processing unit for processing different assigned signals, a storage unit for selectively storing the information of the particular signal processing unit, and an audio and video output unit for outputting the particular signals;

the signal acquisition unit comprising an entertainment signal acquisition unit for acquiring an entertainment signal, and a physiological parameter signal acquisition unit for acquiring physiological characteristics of monitored patients;

wherein the particular signal processing unit comprises an entertainment signal processing unit for processing the signals acquired by the entertainment signal acquisition unit, a parameter signal processing unit for processing the information of the physiological parameters acquired by the physiological parameter signal acquisition unit, and an alarm signal processing unit for judgment according to the processing result of the parameter signal processing unit;

wherein the entertainment signal processing unit comprises an entertainment signal reception unit, an entertainment apparatus initiation unit and a signal judgment unit; the entertainment signal data is received by the entertainment signal reception unit and is then differentiated by the signal judgment unit in order to determine whether the data is single audio signal data, or single video signal data or the data of both audio and video, and an apparatus initiating signal is input to the corresponding audio and video output unit according to the result of the signal judgment unit;

wherein the audio and video output unit comprises a monitor specific display apparatus and a monitor specific loudspeaker which are connected with a signal output end of the alarm signal processing unit, and an entertainment specific playing display apparatus and an entertainment specific loudspeaker which are connected with the entertainment apparatus initiation unit;

wherein the alarm signal processing unit for processing the alarm information of the physiological characteristics comprises an alarm detection unit for detecting the values of the physiological characteristics, an alarm judgment unit embedded with a threshold of the physiological characteristic, an alarm initiation controlling unit connected with a control signal output end of the alarm judgment unit, and an alarm storage unit for storing the information of the occurring alarm and the current measurement values;

wherein the alarm detection unit detects the values of the physiological characteristics in real-time, the alarm judgment unit judges whether alarm occurs, and if the alarm occurs, the alarm initiation controlling unit initiates an alarm lamp, an alarm specific loudspeaker and a screen character prompt; after the alarm occurs, the alarm storage unit stores the information of the occurring alarm and the current parameter measurement values, and once the alarm condition disappears, the alarm in any form is canceled;

wherein the entertainment signal acquisition unit comprises a television signal acquisition unit for acquiring television signals, a broadcast signal acquisition unit for acquiring broadcast signals, a network signal acquisition unit for acquiring network signals, and a disc video/audio signal acquisition unit for acquiring disc video/audio signals;

wherein the patient monitor having entertainment functions further comprises a remote control command receiving/transmitting and operating device in signal interaction with the signal reception unit, and configured for transmitting a remote control command or receiving a state signal returned by the signal reception unit;

wherein the monitor specific display apparatus and the entertainment specific playing display apparatus are double-screen display apparatuses, the double-screen display apparatus comprises a first display panel configured as a monitor specific display screen, a second display panel configured as an entertainment specific display screen, and a connection shaft for connection of the two display panels, wherein the connection shaft comprises a first shaft component rotatably pivoted with the first display panel and a second shaft component rotatably coupled to the second display panel, the second shaft component extends from the first shaft component so as to be vertical to the first shaft component; the connection shaft is connected to between one corner of the first display panel and one corner of the second display panel, and the double-screen display apparatus further defines a first shaft accommodation groove formed at the second display panel to receive a part of the first shaft component, and a second shaft accommodation groove formed at the first display panel to receive a part of the second shaft component, the double-screen display apparatus comprises at least one magnet assembled at the edges of the fast display panel and the second display panel so that the first display panel and the second display panel can be adhered with each other;

the double-screen display apparatus comprises: an external adapter module, a loop module, a display module and a signal input module, the loop module comprises a boosting board and a micro-control processor, the external adapter module supplies power to the boosting board and the micro-control processor, the display module comprises the first display panel and the second display panel, the boosting board provides working voltage for the display module, the display module simultaneously receives and displays the signals provided by the micro-control processor, the signal input module is connected with the micro-control processor, and the micro-control processor processes signals input by the signal input module and controls the first display panel and the second display panel respectively;

the double-screen display apparatus comprises combination sensors which are correspondingly installed on the corresponding positions of the first display panel and the second display panel respectively and which sense whether the two display panels are combined, the combination sensors are in signal interaction with the micro-control processor, and the micro-control processor further comprises a combination image processing unit in signal interaction with the combination sensors, and a combination image judging and selecting unit in signal interaction with the entertainment signal processing unit and a parameter signal processing unit as well as the combination sensors;

wherein when the combination sensors sense that the two display panels are at a combination position, the combination image processing unit regulates an original single-screen display resolution to a combined screen display resolution which is suitable for double-screen combination;

and simultaneously, according to the judged and selected signals from the combination image judging and selecting unit, original display contents on the original first or second display panel are taken as the display contents of the entire screen subsequent to combination;

when a position of the second display panel for displaying the entertainment of physiological characteristics of patient is unchanged, the original contents on the first display panel are displayed subsequent to combination;

and when position of the first display panel for displaying the information of physiological characteristics of patient is changed, and the position of screen for displaying entertainment contents is not changed, the original contents displayed on the second display panel are displayed subsequent to combination.

2. The patient monitor having entertainment functions according to claim 1, characterized in that, the remote control command receiving/transmitting and operating device is an intelligent learning-type remote controller having infrared/radio frequency transmission and reception functions; and wherein the intelligent learning-type remote controller comprises a central processing unit, and a keyboard, a display unit, a wireless communication unit and a storage unit which are connected with the central processing unit, the storage unit is used for storing description files of household appliances; the wireless communication unit comprises an infrared module for code matching learning with controlled electric and electrical equipments having infrared recognition control function, and a radio frequency module for transmitting a control command; and wherein the keyboard and the display unit are used for offering a man-machine interactive interface;

and wherein a control command reception and processing module in the remote control command receiving/transmitting operating device is a reception module capable of receiving infrared/radio frequency signals.

* * * * *